United States Patent [19]
Blumenfeld et al.

[11] Patent Number: 5,306,236
[45] Date of Patent: Apr. 26, 1994

[54] NEEDLE ELECTRODE FOR USE WITH HYPODERMIC SYRINGE ATTACHMENT

[75] Inventors: Arthur Blumenfeld, Brewster; Alan J. Schaefer, Spring Valley, both of N.Y.

[73] Assignee: Vickers PLC, London, England

[21] Appl. No.: 19,077

[22] Filed: Feb. 18, 1993

[51] Int. Cl.$^5$ ............................................. A61N 1/30
[52] U.S. Cl. .................................. 604/21; 604/239; 604/272; 607/116; 128/733
[58] Field of Search ............... 604/187, 239, 272, 20, 604/21; 128/733, 741; 606/32, 44; 607/2, 3, 48, 115, 116

[56] References Cited

U.S. PATENT DOCUMENTS

| | | |
|---|---|---|
| 3,078,850 | 2/1963 | Schein et al. ............... 604/187 X |
| 3,313,293 | 4/1967 | Chesebrough et al. . |
| 3,682,162 | 8/1972 | Colyer . |
| 4,155,353 | 5/1979 | Rea et al. . |
| 4,233,991 | 11/1980 | Bradely et al. ............... 128/733 |
| 4,515,168 | 5/1985 | Chester et al. . |
| 4,711,248 | 12/1987 | Steuer et al. ............... 128/748 |
| 4,824,433 | 4/1989 | Marz et al. . |
| 4,892,105 | 1/1990 | Prass . |
| 5,007,902 | 4/1991 | Witt ............... 604/117 |
| 5,161,533 | 11/1992 | Prass et al. ............... 128/639 |

FOREIGN PATENT DOCUMENTS 0158397 10/1985 European Pat. Off. ............ 604/741

OTHER PUBLICATIONS

Webster's Ninth New Collegiate Dictionary, Merriam-Webster Inc. 1990 pp. 100, 820.

*Primary Examiner*—C. Fred Rosenbaum
*Assistant Examiner*—Mark Bockelman
*Attorney, Agent, or Firm*—Charles E. Baxley

[57] ABSTRACT

An improved needle electrode for use with a hypodermic syringe attachment which includes a needle member, a conductor wire directly attached to an uninsulated portion of the needle member, insulating material formed around at least a portion of the needle member and the conductor wire thereby to form a handle which has a smooth external configuration preferably of ogival shape for easy gripping and dexterous manipulation by an operator. The hypodermic syringe attachment is capable of connection to the handle and an electric lead is capable of connection to the conductor wire. The insulating material is directly formed, as by molding, around the needle member and the conductor wire.

3 Claims, 3 Drawing Sheets

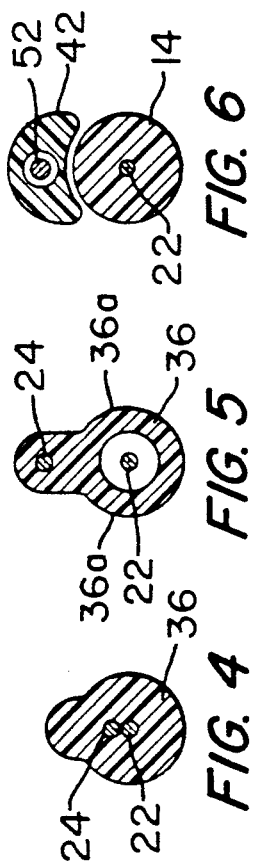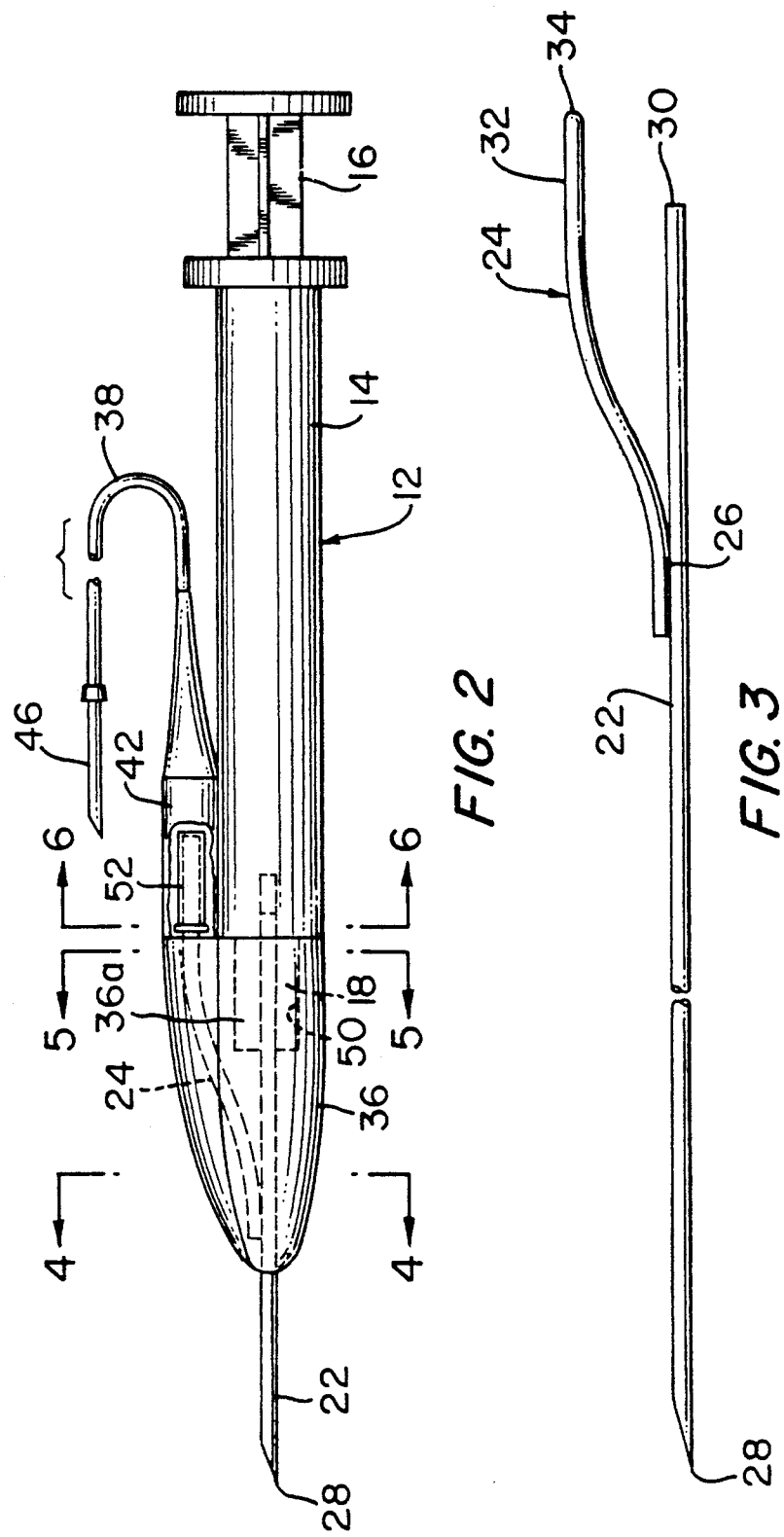

NEEDLE ELECTRODE FOR USE WITH HYPODERMIC SYRINGE ATTACHMENT

BACKGROUND OF INVENTION

This invention relates to an improved needle electrode for use with a hypodermic syringe attachment. More particularly the invention relates to a needle electrode for use in electromyography (EMG) in situations wherein it is desired to insert an electrode, in the form of a probe, into a patient to locate a particular muscle and then inject a medicament into that muscle.

Relevant prior art teaches a hypodermic needle with an open lumen, designed for muscle stimulation, muscle motor unit action potential recording, and drug delivery. A physician locates an exact position of the tip of the needle by either recording or stimulating the muscle. Once the physician is satisfied with the location, s/he injects a drug therein via the lumen of the needle. It is known to perform this procedure using a hypodermic needle coated with Teflon (tetra fluoroethylene), except at the cutting faces, in a standard Luer lock hub or connector. A cable with a very rudimentary clip has been supplied for attachment to a square part of the Luer lock connector.

A state-of-the-art search hereon has revealed the following six (6) pertinent prior United States patents:

| PATENT NO. | DATE | INVENTOR(S) |
| --- | --- | --- |
| 3,313,293 | April 11, 1967 | Chesebrough et al. |
| 3,682,162 | August 8, 1972 | Colyer |
| 4,155,353 | May 22, 1979 | Rea et al. |
| 4,515,168 | May 7, 1985 | Chester et al. |
| 4,824,433 | April 25, 1989 | März et al. |
| 4,892,105 | January 9, 1990 | Prass |

Of the foregoing patents, those to Chesebrough et al. and Colyer appear to come closer than any of the others to the present invention.

Chesebrough et al. discloses an electromedical needle having a slender conductive rod with a pointed end and a blunt end. Insulators and conductors are disposed on selected portions of the rod to form a plurality of longitudinal electrodes insulated from each other. A multi-contact connector is attached to the blunt end of the rod, and shielded cables connect the contacts of the connectors with the ends of the electrodes closest thereto.

Colyer relates to a combined electrode and hypodermic syringe needle. FIG. 5 of Colyer shows a syringe/electrode which is partly encapsulated in a molded sleeve of sterilizable thermosetting plastic material. The sleeve of Colyer extends over a major portion of hub portions 19 and 24, these being Luer fittings and for about half the length of an outer needle 25. In use the needle is connected with an electronic locator/stimulator and inserted into a patient. By means of well known techniques, location and identification of a sensory nerve or a motor nerve is achieved. A syringe is then attached to the needle and medicament is injected as required.

In order to form the electrical connection in Colyer, some kind of form would have to be provided into which handle material would be cast. The form would then have to be removed, leaving a terminal aperture.

It is an important object of the present invention to provide a needle electrode, for use with a hypodermic syringe attachment, that is of simplified construction.

It is another important object of the invention to provide a needle electrode, for use with a hypodermic syringe attachment, that is easier to use than devices of the prior art.

It is another important object of the invention to provide a needle electrode, for use with a hypodermic syringe attachment, wherein a conductor wire is directly attached to the needle member.

It is another important object of the invention to provide a needle electrode, for use with a hypodermic syringe attachment wherein the hypodermic syringe attachment is directly attached to a handle thus eliminating the Luer fitting that is required in the design of the Colyer device.

It is yet another important object of the invention to provide an improved method of manufacturing a handle member for a needle electrode.

The foregoing and other objects and advantages of the invention will appear more clearly hereinafter.

SUMMARY OF THE INVENTION

The invention is a needle electrode for use with a hypodermic syringe attachment. The attachment includes a conductive needle member, a conductor wire attached directly to an uninsulated portion of the needle member, insulating material formed around at least a portion of the needle member and the conductor wire thereby to form a smooth, preferably ogive shaped handle for convenient and accurate positioning and manipulation of the needle electrode. The handle has means for connection thereto of the hypodermic syringe attachment and means for connecting an electric lead to the conductor wire.

In a method aspect, insulating material is directly formed, as by molding, around the needle member and the conductor wire to form the handle.

DESCRIPTION OF THE DRAWING

FIG. 2 is an elevational view of the embodiment of FIG. 1;

FIG. 3 is a view of a connector wire and needle assembly that is an element of the embodiment of FIG. 1;

FIG. 4 is a view on line 4—4 of FIG. 2;

FIG. 5 is a view on line 5—5 of FIG. 2; and

FIG. 6 is a view on line 6—6 of FIG. 2.

DESCRIPTION OF THE INVENTION

Figure 1:
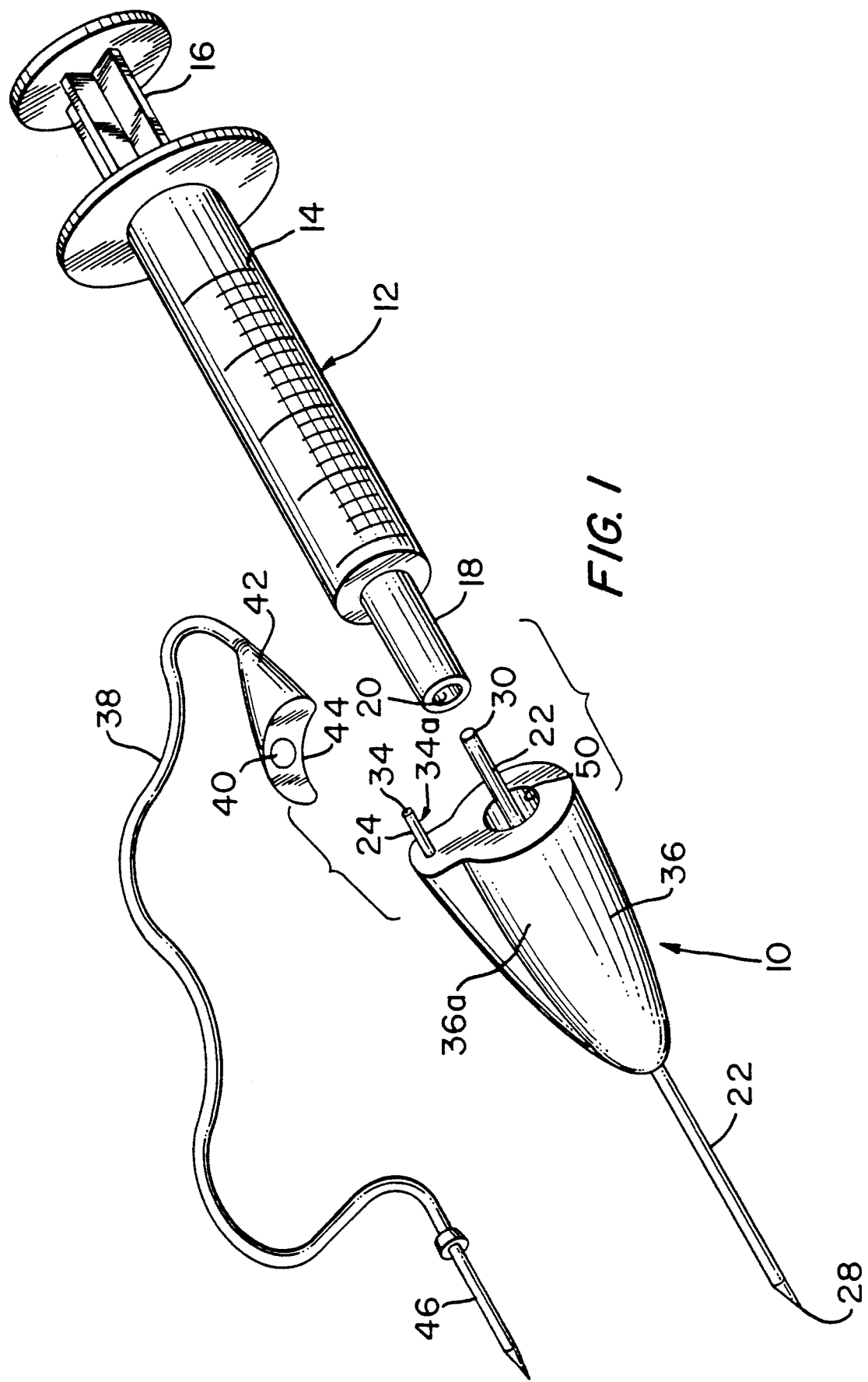
FIG. 1 is a perspective exploded view of the various elements of a first preferred embodiment of the invention.

A first preferred embodiment of the invention will be described here with initial reference to FIG. 1, which shows a needle electrode generally designated 10 in accordance with the present invention for use with a hypodermic syringe attachment 12 which is conventional. The syringe has a cylindrical body 14 of predetermined outside radius, a plunger 16 and a forwardly extending annular nosepiece 18 which is part of a body 14 and which has a cylindrical opening 20.

The needle electrode 10 has a tubular hollow needle member 22 of electrically conductive material, such as stainless steel, and a conductor wire 24 in direct electrically conductive engagement with an uninsulated portion of the needle member 22, as best seen in FIG. 3. The needle member 22 and the conductor wire 24 are secured together (as by soldering or welding) at a location 26. The needle member 22 is straight and extends between a point 28 at a front end and an open rear end 30. The conductor wire 24 o extends rearwardly, preferably in a flat S-shaped curve, from the location 26 to a free end portion 32 that is substantially parallel to the needle member 22 and terminates at a free rear end 34 thus providing a rearwardly facing electrical connection as best seen in FIG. 1. The end portion 32 is spaced from the needle member 22 a distance that is greater than the outside radius of the body 14 of the syringe attachment 12.

Insulating material such as polypropylene is formed as by molding around at least a portion of the needle member 22 and the conductor wire 24 thereby to form a handle 36 for convenient and accurate positioning and manipulation of the needle electrode 10. Physical integration of the handle 36, the needle 22 and the conductor wire 24 is at the core of the invention. The handle 36 has a smooth external configuration 36a for easy gripping and manipulation by an operator (the physician). Preferably, and as shown particularly in FIGS. 1 and 4, the external configuration of the handle is ogive-like for ease, comfort and dexterity of handling, as well as for delicate and accurate manipulation.

As best seen from FIG. 5 material formed around the conductor wire 24 is blended tangentially with material formed around the needle 22 to form the handle 36 with slightly enlarged flat side gripping areas 36a. The bulge or ridge 36b is best seen in FIGS. 4, 5, and 6.

The handle 36 includes means for connection thereto of the hypodermic syringe attachment 12 and means for connecting an electric lead 38 to the conductor wire 24. Connecting means are shown in FIG. 1 as a socket connector element 40 adapted releasably to receive therein the free end 32 of the connector wire 24. The connector element 40 is located within a smoothly contoured insulating body 42 having a cylindrically concave inwardly facing surface 44 configured to have a radius of curvature substantially the same as the outside radius of curvature of the cylindrical body 14 of the syringe attachment 12. Thus, the lead 38 can be connected readily and releasably electrically to the connector wire 24 with the connector element 40 receiving the free end 32 of the connector wire 24, and with the nosepiece 18 of the syringe attachment 12 receiving the needle member 22, so that the concave cylindrical surface 44 of the insulating body 42 fits closely over the cylindrical body 14 of the syringe attachment 12. Lateral displacement of the conductor wire 24 enables free end portion 34 of connector 24 to maintain a parallel relationship with the needle 22 and terminates in rearwardly facing electric connection which allows the handle portion 36 to be formed with a main gripping area 36a relatively remote from the electrical connection 34. Thus the main gripping area 36a and bulge or ridge 36b can be made free of outwardly projecting terminals and leads, unlike the prior art Colyer device mentioned above. With the present invention there is little chance of the electrical connection being disturbed during manipulation of the needle with consequent degradation in signal. The other end of the, lead 38 has a fitting 46 for attachment to an electrical supply (not shown).

Figure 7:
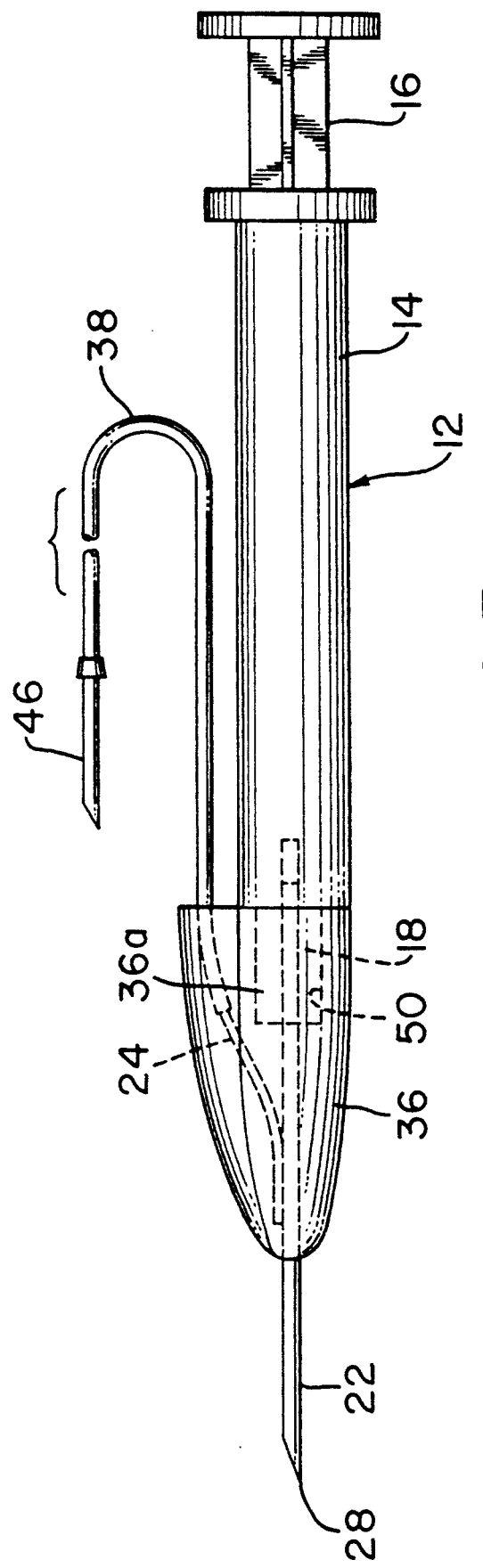
FIG. 7 is an elevational view of a second preferred embodiment of the invention with an umbilical wire molded into the nosepiece.

In the second preferred embodiment shown in FIG. 7 an umbilical electric lead 38 is embedded in the body 36 and is an extension of the conductor wire 24. The umbilical electric lead 38 terminates in the usual manner in an electrical fitting 46. By this embodiment the relatively short lead 38 can be sterilized easily along with the needle assembly to which it remains attached. In this embodiment it is easier to keep the field sterile. The integral connection of connector wire 24 to the needle 22 and to the lead 38 provides a robust assembly which is more resistant o movement and electrical disturbance.

The rearward end of the handle 36 has a well 50 adapted for snug receipt therein of the nosepiece 18 of the syringe attachment 12. When the syringe attachment 12 is assembled with the handle 36 as described above and as shown in the drawings, medicament in syringe attachment 12 can be injected into open end 30 of hollow needle 22 and thereby into the patient. Despite the fact that nose piece 18 is merely a snug sliding push fit within well 50 it has been shown, somewhat surprisingly, that fluid connection between needle electrode 10 and the syringe attachment 12 remains intact despite considerable internal pressure that is generated when the medicament is being injected. The electric lead 38 can readily be connected to and disconnected from the conductor wire 24.

The insulating body 42, a suitable material for which is polypropylene, contains a fitting 52 (FIG. 2) adapted for releasably joining the end 34 of the conductor wire 24 and the electrical lead 38.

It is also significant, from the standpoint of operator comfort, accuracy and dexterity, that the bulge or ridge 36b of the handle 36 and the exterior surface of insulating body 42 are smooth continuations of each other when the bulge or ridge 36b and the insulating body 42 are assembled. See FIGS. 2, 5 and 6.

It is apparent that the invention well attains the aforesaid objects and advantages, among others. The disclosed details are exemplary only and are not to be taken as limitations on the invention except as those details may be included in the appended claims.

We claim:

1. A needle electrode, for use with a hypodermic syringe, the electrode comprising:

a hollow straight needle of electrically conductive material with an axis and a tip end and a rear end, a conductor wire connected fixedly to the needle and extending radially outwardly and rearwardly therefrom, insulating material formed around the grip portion of the handle and the conductor wire to provide a firm solid handle, said grip portion sufficiently long for an operator's thumb and first two index fingers of one hand to grasp comfortably the handle like a writing instrument, said grip portion arranged to maintain the operator in electrical isolation from the needle, the handle provided with an external configuration that is ogival in shape from a rounded nose situated toward the tip end to a divergent rear adapted to receive the syringe in fluid flow communication with the needle, the handle provided with electrical engagement means for connecting a source of electricity to the conductor wire, the electrical engagement means comprising a smoothly contoured insulating body having a cylindrically concave inwardly facing surface rearward of said grip portion of the needle and adapted in use to be configured with the syringe in a smooth convex profile which is a continuation of the ogival configuration of the handle.

2. The needle electrode as claimed in claim 1 wherein the conductor wire terminates in a rearwardly facing electrical connection behind said grip portion of the needle.

3. The needle electrode as claimed in claim 2 with the electrical engagement means detachably connectable to the conductor wire.

* * * * *